United States Patent [19]

Khanna

[11] Patent Number: 4,504,413

[45] Date of Patent: Mar. 12, 1985

[54] ACETAMINOPHEN ANALOGS, ANTIGENS, AND ANTIBODIES

[75] Inventor: Pyare Khanna, San Jose, Calif.

[73] Assignee: Syva Company, Palo Alto, Calif.

[21] Appl. No.: 552,955

[22] Filed: Nov. 17, 1983

Related U.S. Application Data

[62] Division of Ser. No. 364,836, Apr. 2, 1982, Pat. No. 4,424,150.

[51] Int. Cl.³ .................. C07C 101/44; A61K 31/015
[52] U.S. Cl. ........................ 260/112 R; 260/112.5 R; 424/94; 560/19; 560/23; 560/43; 560/51
[58] Field of Search .................. 260/112 R, 112.5 R; 424/94, 233, 324, 330; 560/19, 23, 43, 51; 435/128, 129

[56] References Cited

U.S. PATENT DOCUMENTS

| | | | |
|---|---|---|---|
| 3,975,342 | 8/1976 | Gross | 260/112 B |
| 3,981,863 | 9/1976 | Niswender et al. | 260/112 R |
| 4,181,719 | 1/1980 | Margetts et al. | 560/142 |
| 4,212,878 | 7/1980 | Lednicer et al. | 564/170 |
| 4,256,669 | 3/1981 | Benner et al. | 564/434 |

Primary Examiner—John Kight
Assistant Examiner—Nathan M. Nutter
Attorney, Agent, or Firm—Bertram I. Rowland; Theodore J. Leitereg

[57] ABSTRACT

Carbonyl derivatives of acetaminophen are provided for use in homogeneous enzyme immunoassays for acetaminophen. The derivatives are conjugated to antigenic substances for the preparation of antisera specific to acetaminophen, and to enzymes for the preparation of enzyme conjugates which compete with acetaminophen for antibody binding sites in a typical assay.

11 Claims, No Drawings

ACETAMINOPHEN ANALOGS, ANTIGENS, AND ANTIBODIES

This is a division of application Ser. No. 364,836 filed Apr. 2, 1982, now U.S. Pat No. 4,424,150.

BACKGROUND OF THE INVENTION

1. Field of the Invention

N-acetyl-p-aminophenol, commonly known as acetaminophen, is known a wide variety of uses, e.g., as an intermediate for pharmaceuticals and azo dyes, as a stabilizer for hydrogen peroxide, as a photographic chemical, and as a medicinal drug. Its medicinal use is the most well known, notably as a non-prescription analgesic with properties similar to aspirin. It is thus used as the active ingredient in the preparations designated paracetamol (U.K.) and Tylenol ® (U.S.), and as a major component in over 200 other drug formulations.

While it has several advantages over aspirin, notably a lesser tendency to promote internal bleeding, acetminophen has unfortunately been found to exhibit hepatotoxic properties when present in large quantities in the blood stream. As a result, acetaminophen overdose has become a frequent method of suicide in recent years. Death can be avoided by the administration of an antidote, but only if the antidote is administered within 10 to 12 hours of acetaminophen ingestion. Thus, it is of the utmost importance that the acetaminophen level is the blood plasma or other bodily fluids be determined within a few hours ingestion.

Currently known assay methods include colorimetry, UV spectrophotmetry, gas liquid chromatography, high pressure liquid chromatography, fluorometry, and voltametry. Colorimetry requires either the conversion of the acetaminophen to p-aminophenol, or a dye reaction, or nitration. These are time-consuming procedures, and the accuracy of this method suffers from the potential interference of similar drugs present in the sample. UV spectrophotometry, fluorometry, and voltametry similarly suffer from interference, notably from salicylate and other compounds with phenolic hydroxy groups. While such interference can sometimes be elimated by splitting the sample into two parts, acidifying one and rendering the other alkaline, the procedure is still time-consuming and labor-intensive. Gas and liquid chromatography are similarly time-consuming and labor-intensive, with the further disadvantage of requiring highly specialized instrumentation.

In addition to acetaminophen itself, various metabolized forms of the drug are normally present in the body fluid to be analyzed, further complicating the detection procedure. These metabolites include the glucuronide and the sulfate (each with the modifying moiety substituting for the hydroxyl hydrogen), as well as the cysteine and mercapturic acid conjugates (in each of which the added group is positioned at the C-3 ring position, i.e., the position adjacent to the position occupied by the hydroxyl group). A normal dosage of acetaminophen is 80%-90% metabolized in the liver to form the first two of these metabolites, with the rest going to the last two, leaving only about 2% of the acetaminophen unchanged. When a overdose is ingested, the capacity of the liver to form these metabolites is overloaded and the acetaminophen (through its unstable intermediate, N-acetylimidoquinone) binds to hepatocyte proteins. Liver damage and death are caused in this manner, and although such results usually take several days to occur, the antidote is ineffective unless administered during the first 10 to 12 hours. Thus, it is the unchanged acetaminophen itself which must be detected rather than any of the metabolities.

A simple and rapid procedure is therefore needed for determining acetaminophen levels in serum or other physiological fluids, which provides reproducible values and is specific for acetaminophen.

2. Description of the Prior Art

Acetaminophen, its metabolism, and its hepatotoxic properties are disclosed in Wiener, K., *Annals of Clinical Biochemistry,* vol. 15, p. 187 (1978); Liu, T., et al., *Clin. Chem.,* vol 26, p. 69 (1980); Knox, J. H., et al., *Journal of Chromatograph,* vol. 149, p. 297 (1978); and Davis, M., et al., *Journal of International Medical Research,* vol. 4, p. 40 (1976). The first two of these references also disclose existing analytical techniques for measuring acetaminophen levels in serum and their inherent limitations. Homogeneous enzyme immunoassay techniques are described in Rubenstein, et al., U.S. Pat. No. 3,817,837, issued June 18, 1974 (Syva Co.).

SUMMARY OF THE INVENTION

Carbonyl derivatives of acetaminophen are provided as precursors to protein conjugates, where the proteins are antigens or enzymes. The antigens are used for production of antisera to acetaminophen, which antisera together with the enzyme conjugates are used as reagents in sensitive specific immunoassays for monitoring acetamiophen levels in biological fluids. The resulting immunoassays offer a high degree of sensitivity and reproducibility together with a low degree of interference from the large number of both chemically similar and diverse compounds which are frequently present in the same fluids.

DESCRIPTION OF THE SPECIFIC EMBODIMENTS

The present invention relates in novel reagents for use in diagnostic immunoassays for acetaminophen. These reagents include acetaminophen analogs, antigenic conjugates and the antisera prepared therefrom, and acetaminophen analog-enzyme conjugates formed by replacing the methyl group on the N-acetyl portion of acetaminophen with a linking group to a carboxylic acid moiety, or by attaching an amidoalkylcarboxyl group at the C-2 ring position (adjacent to the acetamido group). The resulting reagents are used in an immunoassay system which is capable of measuring extremely low levels of acetaminophen with substantially no interference from similarly structured compounds.

Specifically, the novel reagents are compounds having the following forumla:

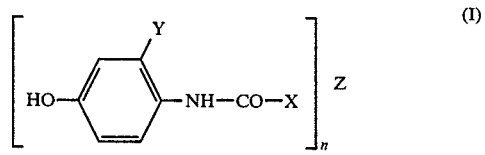

wherein:

X is methyl or $-R-(CO)_m$

Y is $-R^1-CO-HN-R^2-(CO)_m$ when X is methyl, and hydrogen when X is $-R-(CO)_m$ R, $R^1$ and $R_2$ are independently aliphatic hydrocarbon linking groups of straight- or branched-chain configuration, of from 1 to 12 carbon atoms each, preferably having no more than one site of aliphatic unsaturation, more preferably being fully saturated, and most preferably having a straight-chain configuration (i.e., a polymethylene group);

Z is hydrogen, hydroxyl, alkoxyl of from 1 to 6 carbon atoms, preferably from 1 to 3 carbon atoms, a group capable of forming an activated ester capable of amide formation with an amino acid in an aqueous medium, or a poly(amino acid) residue, either a polypeptide or protein, having one or more subunits and having a molecular weight of at least about 5000, preferably from about 10,000 to about 1,000,000 daltons, functioning as either an antigen or an enzyme;

m is zero or one when Z is a poly(amino acid) residue, and is otherwise one; and when Z is a poly(amino acid) residue, n is an integer ranging from one to a value approximately equal to the molecular weight of Z divided by 500, preferably one to approximately the molecular weight divided by 1,000, more preferably one to approximately the molecular weight divided by 2000, still more preferably one to approximately the molecular weight divided by 3000, and most preferably from about 10 to about 100 when Z is an antigen and from about 1 to about 20, more usually 2 to 20, when Z is an enzyme; and when Z is other than a poly(amino acid) residue, n is one.

In further preferred embodiments, R contains 2 to 8, more preferably 3 to 6 carbon atoms; $R^1$ contains 1 to 6, more preferably 1 to 4 carbon atoms; and $R^2$ contains 1 to 6, more preferably 1 to 3 carbon atoms.

Expressed in a different form, the compounds of the present invention are those provided by the following formulas:

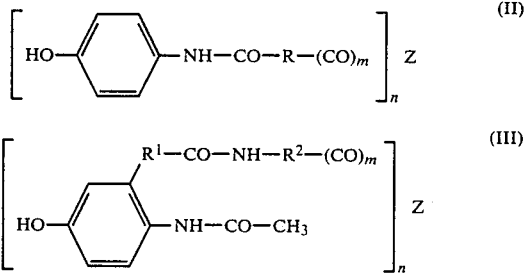

in which R, $R^1$, $R^2$, m, n, and Z are as defined above including all preferred embodiments.

In all of the formulas, when Z is hydrogen, hydroxyl, or alkoxyl, the compounds are acetaminophen analogs useful as precursors from which enzyme conjugates and antigens which will generate antisera specific to acetaminophen can be made. When Z is a poly(amino acid) residue, which can be either an enzyme or an antigen (note also that enzymes may act as antigens), the result is either an enzyme conjugate capable of reacting with the antiserum, or an antigen which will generate antisera specific to acetaminophen.

The poly(amino acids) will generally range from about 5000 molecular weight, having no upper molecular weight limit, normally being not more than 10,000,000, usually not more than about 600,000 daltons. There will usually be different ranges, depending on whether an antigen or an enzyme is involved with antigens ranging from about 5000 to $10^7$, usually from about 20,000 to 600,000, and more usually from about 25,000 to 250,000 daltons; while enzymes will generally range from about 10,000 to 600,000, more usually from about 10,000 to 300,000 daltons.

The number of acetaminophen analogs bound to any given enzyme or antigen will depend on several factor—e.g. the molecular weight of the enzyme or antigen, the degree of labeling desired (from light to heavy), the effect on enzyme activity and inhibitability of varying degrees of labeling, the specific type of enzyme or antigen, etc. Enzyme activity is usually reduced as more analog groups are attached to each enzyme, while inhibitability will usually be enhanced up to some average number of labels. Thus, an optimum analog-to-enzyme ratio exists for each system, the optimum varying with the antisera, the enzyme, the analog, and the range of sample concentration.

Similar considerations exist for the analogs bound to the antigens. With intermediate molecular weight antigens (35,000 to 1,000,000), the number of conjugate groups will generally be from about 2 to 250, more usually from 10 to 100. With lower molecular weight antigens, below 35,000, the number of conjugates will generally be in the range of from abut 2 to 10, usually in the range of 2 to 5.

Various protein types may be employed as the antigenic material. These types include albumins, serum proteins, e.g., globulins, ocular lens proteins, lipoproteins, etc. Illustrative proteins include bovine serum albumin, keyhole limpet hemocyanin, egg ovalbumin, bovine gamma-globulin, etc. Alternatively, synthetic poly(amino acids) may be prepared having a sufficient number of available amino groups, e.g. lysines.

The enzymes can be varied widely, depending upon the rapidity with which one desires a result and the physiological fluid in which the acetaminophen is to be measured. Primarily, the enzymes of choice, based on the I.U.B. classification are Class 1. Oxidoreductases and Class 3. Hydrolases. Particularly in Class 1, the enzymes of interest are dehydrogenases of Class 1.1, more particularly 1.1.1 and 1.1.99 and peroxidases, in Class 1.11. Of the hydrolases, particularly Class 3.1, more particularly 3.1.3 and Class 3.2, more particularly 3.2.1.

Illustrative dehydrogenases include malate dehydrogenase, glucose-6-phosphate dehydrogenase, and lactate dehydrogenase. Of the peroxidases, horse radish peroxidase is illustrative. Of the hydrolases, alkaline phosphatase, β-galactosidase, β-glucosidase and lysozyme are illustrative.

Particularly preferred are those enzymes which employ nicotinamide adenine dinucleotide (NAD) or its phosphate (NADP) as a cofactor, particularly the former. Most preferred as the choice of enzyme is glucose-6-phosphate dehydrogenase.

The compounds of the present invention can be prepared by conventional methods. Those of Formula II are conveniently prepared by reacting an appropriately selected dicarboxylic acid halide monoalkyl ester of the formula Cl-CO-R-$CO_2$R' where R is as defined above and R' is alkyl, with p-aminophenol in the presence of a suitable base (e.g., triethylamine) and a suitable solvent (e.g., tetrahydrofuran) at low temperature. The ester can then be hydrolysed to a carboxylic acid, which if desired, can then be reduced to an aldehyde, both steps by conventional techniques, depending on which type of precursor is sought. Once the precursor is formed, it is combined with the appropriate poly(amino acid) in a conventional manner. This usually consists of first forming a reactive carboxylic acid derivative, e.g., ester, capable of amide formation when contacted with an amino acid in an aqueous medium. Examples of reagents for such activation include p-nitrophenol, N-hydroxy succinimide, carbodiimide and acetic anhydride. Antigens or enzyme conjugates are then generated by reacting the resulting activated acid with the appropriate poly(amino acid).

The compounds of Formula II are conveniently prepared by reacting 2-nitro-5-hydroxybenzaldehyde with a dicarboxylic acid and piperidine in pyridine, followed by treatment with dicyclohexyl carbodiimide and N-hydroxysuccinimide, then triethylamine and t-butylglycine (or an appropriate analog with an alkylene group separating the amino and carboxylate groups) hydrochloride, then reducing the nitro group to an amino group, acetylating both the amino and hydroxy groups, regenerating the hydroxy group using base followed by acid, and finally converting the t-butyl ester moiety to a carboxylic acid moiety. Again, reduction to the aldehyde is optional. Reactive esters, antigens, and enzyme conjugates can then be prepared as described above.

The antigenic conjugates may be injected into a wide variety of vertebrates in accordance with conventional methods for the production of antibodies. Usually, the animals are bled periodically with the successive bleeds improving in titer and specificity until a maximum is reached, followed by a gradual decline. Antibodies are then isolated from the bleeds with the maximum values.

As previously indicated, the antibodies and enzyme reagents prepared in accordance with the subject invention find particular use in immunoassays for the determination of acetaminophen. A description of the method for carrying out the immunoassay, which is a homogeneous enzyme immunoassay, may be found in U.S. Pat. No. 3,817,837, the disclosure of wich is incorporated herein by reference. The method involves combining the enzyme conjugate, the unknown sample suspected of containing acetaminophen, and an antibody for acetaminophen in an aqueous buffered medium at a temperature in the range of about 10° to about 50° C., more usually from about 20° to about 40° C. The enzyme activity is then compared to that of a sample with a known amount of acetaminophen, or with a standard curve.

A wide variety of methods can be used to determine enzyme activity, including many of the conventional techniques known to those skilled in the art. The most appropriate technique for any given assay will depend upon the particular enzyme used. A particularly convenient technique is the use of spectrophotometry, where an enzyme cofactor, a substrate, or the product of enzyme activity on a substrate absorbs light in the ultraviolet or visible region. Other techniques include fluorimetry, viscometry, luminescence measurements, pH measurements, electron spin resonance spectrometry, and the use of ion specific electrodes. A preferred method of applying any such technique is to record the change in signal (either absorbance or some other parameter depending upon the technique used) over a fixed period of time from the initial contact of the components.

The reagents of the present invention are unusual in their ability to provide a highly specific assay for acetaminophen with substantially no interference (cross-reactivity) from other compounds often present in the sample to be analyzed. This includes the various metabolites of acetaminophen as well as a host of other compounds of similar structural formulae, particularly those which are normally expected to induce a similar immune response. A further feature is that different acetaminophen analogs can be used to prepare reagents used in combination in the same assay—i.e., an antibody derived from one acetaminophen analog can be used in combination with an enzyme conjugated to a different acetaminophen analog. In fact, a compound of formula II above can be used together with one of Formula III.

The following examples are offered by way of illustration and not by way of limitation.

EXPERIMENTAL (All temperatures are centigrade unless otherwise indicated. All parts and percentages are by weight, except for mixtures of liquids, which are by volume. The following abbreviations are used:
—THF: tetrahydrofuran; tlc: thin layer chromatography; nmr: nuclear magnetic resonance; UV: ultraviolet; IR: infrared; HOAc: acetic acid; BSA: bovine serum albumin; BgG: bovine gamma-globulin; DCC: dicyclohexyl carbodiimide; NHS: N-hydroxy succinimide; G6P: glucose-6-phosphate; G6PDH: glucose-6-phosphate dehydrogenase; NAD: nicotinamide adenine dinucleotide; NADH: nicotinamide adenine dinucleotide, reduced form; DMF: dimethylformamide; EDAC: ethyl 3-dimethylaminopropyl carbodiimide; RSA: rabbit serum albumin; R: change in optical density over assay time period; $R_o$ change in optical density over assay time period for sample containing no acetaminophen; $R_{max}$: change in optical density over assay time period in absence of antibody (i.e., enzyme uninhibited). Melting points were measured on a Thomas-Hoover capillary melting point apparatus and are reported uncorrected. Analytical tlc was performed on Analtch Uniplate glass plates with a 250-micron thick silica gel coating. Dry THF was distilled over sodium benzophenone ketyl under argon prior to use.)

1.1 Preparation of 5-(4'-Hydroxyanilido)pentanoic acid (Formula II above with R=—CH$_2$CH$_2$CH$_2$CH$_2$—, m=1, n=1, and Z=OH).

Into a suspension of p-aminophenol (1.9 g, 17.5 mmol) and triethylamine (5.0 g, 50 mmol) in THF (80 ml) was added 5 ml of a solution of adipic acid chloride-monomethyl ester (6.25 g, 35 mmol) in THF (10 ml). Analysis by tlc (CH$_2$Cl$_2$/CH$_3$OH)/ HOAc, 85/15/1) indicated complete reaction in 30 min. The reaction mixture was quenced with ice/water, extracted with ether, dried (MgSO$_4$) and evaporated to dryness.

This material was dissolved in 50 ml methanol at 0° and to it was added sodium carbonate (0.5 M, 100 ml, 50 mmol). The reaction mixture was allowed to stir for 17 n, quenched with 1N HCl/ice, extracted with ethyl acetate, dried over Na$_2$SO$_4$, and evaporated to dryness. Analysis by nmr indicated only partial hydrolysis had occurred.

The material was dissolved in methonal (25 ml) and to it was added 1 N NaOH (32 ul). This mixutre was stirred for 27 h at room temperature. Quenching with 1 N HCl/ice followed by extraction with ethyl acetate, washing with a brine solution, drying over Na$_2$SO$_4$, and evaporation to dryness affored a crude solid. Recrystallization from ethyl acetate gave 2.78 g (63%) of 5-(4'-hydroxyanilido)pentanoic acid, with a melting point range of 180°–183°. A tlc analysis (CH$_2$Cl$_2$/CH$_3$OH/HOAc; 85/15/1) showed one major spot, R$_f$=0.7.

Analysis calculated for C$_{12}$H$_{15}$NO$_4$: C, 60.76%; H, 6.33%; N, 5.91%. Found: C, 60.39%; H, 6.36%; N, 5.72%.

1.2 Preparation of BSA Conjugate of 5-(4'-Hydroxyaniliod)pentanoic Acid (adipaminophen)

(In this and all subsequent conjugations, the hapten numbers were determined by comparing the UV spectra of the conjugate with the UV spectra of a series of known mixtures of the same haptens and proteins used in the conjugates. The ratio of the absorbance at the hapten wave-length ($\lambda_{260}$ for adipaminophen) to that at the protein wavelength ($\lambda_{290}$ for BSA) was compared to a standard curve derived from the ratios of the known mixtures.)

Into a solution of 5-(4'-hydroxyanilido)pentanoic acid (95.5 mg, 0.40 mmol) in THF (6 ml) were added DCC (165 mg, 0.80 mmol) and NHS (46 mg, 0.40 mmol). This reaction mixture was stirred at 4° under argon for 8 days. Analysis by tlc (CH$_2$Cl$_2$/CH$_3$OH/HOAc; 85/15/1) showed complete reaction.

The reaction mixture was filtered, evaporated washed with hexane, evaporated and THF (8 ml) added. This solution of the NHS ester was added dropwise to a solution of BSA (400 mg, 6.2 mmol) in phosphate (pH=8.5) buffer (20 ml) at 4° and was stirred for 2 days.

The reaction mixture was centrifuged at 10K and 4° for 30 min, dialyzed against water (1×4 L) for 3 days, chromatographed on Sephadex G-25 (100 g, 500 ml) eluting with pH=8.5 phosphate buffer, dialyzed against water (2×4 L), and lyophilized to afford 456 mg of antigen. The hapten number was determined to be 18.

1.3 Preparation of BgG Conjugate of 5-(4'-Hydroxyanilido)pentanoic acid

The NHS ester of 5-(4'-hydroxyanilido)pentanoic acid (60 mg, 0.26 mmol) was prepared as above, using DCC (103 mg, 0.50 mmol) and NHS (30 mg, 0.25 mmol) in THF (5 ml). After 45 h the reaction was complete according to tlc.

The NHS ester in the THF (5 ml), worked up as previously described, was added dropwise to a solution of BgG (500 mg, 2.86 mmol) in phosphate (pH=9.0) buffer and stirred at 0° for 1 day.

The reaction mixture was dialyzed against water/ammonium hydroxide (pH=10) (3×4 l) for 4 days after which time no residual hapten was found in the water. Centrifugation at 10 K and 4° for 30 min followed by lyophilization afforded 355 mg (63%) of conjugate. The hapten number was determined to be approximately 46.

1.4 Conjugation of 5-(4'-Hydroxyanilido)pentanoic acid to Glucose-6-phosphate Dehydrogenase A reaction flask was charged with 5-(4'-hydroxyanilido)pentanoic acid, NHS, and EDAC in a sufficient amount of dry DMF to produce a solution of the following composition: 5-(4'-hydroxyanilido)pentanoic acid, 0.1M; NHS, 0.1M; EDAC, 0.115M. The vessel was then flushed with argon and cooled to 4° with constant stirring. The formation of the NHS ester was complete within 16 h, as determined by tlc.

A 3 mg/ml solution of G6PDH (Worthington Lot L03, 10 ml) in 0.055M tris-HCl buffer (pH=8.1) was combined with 200 mg of G6P disodium salt, 400 mg of NADH, and 3.0 ml of DMF. The resulting solution was stirred at 4°, and 0.1M solution of the NHS ester was added in increments over several hours. The final pH of the solution was 9.0. During the addition, the enzyme activity was monitored in accordance with the procedure described below to determine percent activation. Percent inhibition by antibody reaction was also determined, by adding excess antiserum (prepared by the procedure described below) and measuring the remaining enzyme activity.

TABLE I

| G6PDH Conjugation of 5-(4'-Hydroxyanilido)pentanoic acid | | | |
|---|---|---|---|
| Total Hapten Added (μl) | Hapten/Enzyme Mole Ratio | Percent Deactivation* | Percent Inhibition |
| 0 | 0 | — | ) |
| 45 | 16 | 32.8 | 3 |
| 100 | 35 | 71.5 | :0 |
| 133 | 46 | 34.0 | 40 |

*Average of results obtained using four different antiserum bleeds (see below)

The figures in this table indicate that a readily detectable response can be achieved with conjugates having hapten/enzyme ratios well below 100. This indicates a highly efficient conjugation.

Desalting of the product was achieved by dialysis against basic buffer at 4° C. Three changes of buffer were made over four days, using a 200–400x sample-to-buffer ratio each time. Yield after dialysis was sufficient for the preparation of 4 liters of conjugate solution from 30 mg (20,340 units) of G6PDH, with a hapten-to-enzyme mole ratio of approximately 80:1.

2.1 Preparation of N-([3-(2'-Acetylamino-5'-hydroxyphenyl-1')]propionyl glycine (Formula III above with R$^1$=—CH$_2$CH$_2$—, R$^2$=—CH$_2$, m=1, n=1, and Z=OH).

Into a solution of 2-nitro-5-hydroxy-benzaldehyde (8.35 g, 50 mmol) and piperidine (2.135 g, 25 mmol) in pyridine (50 ml) was added malonic acid (10.4 g, 100 mmol). The reaction mixture was heated to reflux (100°) and stirred for 4 h.

After cooling, the reaction mixture was poured into 1 N HCl/ice (pH=1.0), extracted with ethyl acetate, dried over Na$_2$SO$_4$ and evaporated to dryness. Recrystallization from methanol/ethyl acetate afforded 7.065 g (67.6%) of 2-nitro-4-hydroxy-trans-cinnamic acid in two crops.

To a solution of 7.0 g, 39.5 mmol, of this material in THF (100 ml) under argon at room temperature was added DCC (14.42 g, 70 mmol) and NHS (8.05 g, 70 mmol). The reaction mixture was stirred for 24 h, then filtered under vacuum. The cake was then washed with dry THF, and the filtrate was evaporated, washed with hexane, evaporated, dissolved in THF (100 ml) and refiltered. The resulting solution was added dropwise to a solution of the t-butyl ester of glycine hydrochloride (8.55 g, 51 mmol) and triethylamine (13.2 g, 130 mmol) in THF (50 ml) at 0° under argon over 20 min. Stirring was continued for 4 days with the temperature warming to 25°.

The reaction mixture was poured into HCl/ice (pH=2) and extracted with ethyl acetate (800 ml). The ethyl acetate layer was filtered under vacuum, the filtrate was evaporated to 200 ml, and methanol (20 ml) was added. The organic layer was extracted with 1N NaOH, and the aqueous layer was acidified with ice/HCl and extracted with ethyl acetate (800 ml). The organic layer was dried over $Na_2SO_4$, concentrated and crystallized from ethyl acetate to afford 7.87 g (68.9%) of the 2-nitro-4-hydroxy-trans-cinnamic acid amide of t-butyl glycinate in two crops as a yellow solid.

A dissolved suspension of the above amide (5.0 g, 16.2 mmol) and $PtO_2$ (0.73 g, 3.2 mmol) in methanol (150 ml) was flushed with argon for 10 min, then three times with hydrogen at 30 psi and hydrogenated at 55 psi and 30° for 1 h. The reaction mixture was filtered through Celite ®, dried over $Na_2SO_4$ and evaporated to afford 4.5 g (98%) of the amide of t-butyl glycinate of 2-amino-4-hydroxy-trans-cinnamic acid as a yellow solid.

A solution of 3.12 g, 11.1 mmol, of this material and 2.02 g, 20 mmol, of triethylamine in 21.6 g, 212 mmol of acetic anhydride was stirred at room temperature for 5 min. It was then cooled to 4° with an ice bath and 2.0 g, 20 mmol, of triethylamine was added. The reaction mixture was stirred for 40 min, quenched with methanol (20 ml), evaporated, dissolved in ethyl acetate, washed with 1N HCl, washed with saturated brine, dried over $Na_2SO_4$, and evaporated to dryness. This material was hydrolyzed without further purification. Analysis by tlc ($CH_2Cl_2$/MeOH; 9/1) showed one new spot of higher $R_f$ than the material of the preceding paragraph.

A solution of 3.9 g, 10.7 mmol, of the material just formed, in methanol (20 ml) and 1N NaOH (50 ml), was stirred at 4° for 1.5 h, poured into 1N HCl/ice (100 ml), extracted with ethyl acetate, dried over $Na_2SO_4$, and evaporated to dryness for 3 days to afford a crude solid. The solid was dissolved in ethyl acetate, washed with carbonate/ bicarbonate/HCl (pH=7.3) buffer, and evaporated to dryness to afford 2.31 g (67%) of the 2-acetylamino-4-hydroxy-trans-cinnamic acid amide of t-butylglycinate.

A solution of 2.3 g, 7.17 mmol, of this material and 22.2 g (15 mmol) of trifluoroacetic acid was stirred under argon at 4° and was allowed to warm to 25° over 30 min. The reaction mixture was evaporated under vacuum and elthy acetate was added to precipitate the product. The suspension was then heated to reflux and methanol was added dropwise until the solution became homogeneous. Crystals formed upon cooling. Filtration of the solid followed by recrystallization of the mother liquor afford 1.88 g (99%) of N-[3-(2'-acetylamino-5'-hydroxyphenyl-1')]propionyl glycine in two crops. Analysis by tlc ($CH_2Cl_2$/$CH_3OH$/HOAc; 9/1/0.1) showed 1 spot, $R_f \approx 0.2$. The melting point was 159°–162° C.

Analysis calculated for $C_{13}H_{16}N_2O_5$: C, 55.71%; H, 5.71%; N, 10.00%. Found: C, 55.68%; H, 5.74%; N, 9.92%.

2.2 Preparation of BSA Conjugate of N-[3-(2'-Acetylamino-5'-hydroxyphenyl-1')]propionyl glycine.

To a solution of the compound prepared in Example 2.1 (133 mg, 0.47 mmol) in THF (10 ml) at 0° were added DCC (103 mg, 0.50 mmol) and NHS (58 mg, 0.50 mmol) under argon. The temperature rose to 25° and the reaction mixture was stirred for 1.75 h, after which time the reaction was cooled to 4° and stirred for an additional 17 h.

The NHS ester was filtered, evaporated, washed with hexane, and evaporated again. THF (10 ml) was then added and the resulting solution was added dropwise to a cold stirring solution of BSA (500 mg, 7.77 μmol) in phosphate buffer (pH=8.5) was allowed to react at 4° for 23 h.

The reaction mixture was dialyzed against water/ammonium hydroxide (2×4 L), centrifuged at 10 K and 4° for 30 min, chromatographed on Sephadex G-25 (100 g, 500 ml), dialyzed against water/ammonium hydroxide (3×4 L) for 4 days and lyophilized to afford 476 mg (75.6%) of conjugate. The hapten number was determined to be 16.

2.3 Preparation of BgG Conjugate of N-[3-(2'-Acetylamino-5'-hydroxyphenyl-1')]propionyl glycine.

The NHS ester of the compound prepared in Example 2.1 (68 mg, 0.24 mmol) was prepared as described above via reaction with DCC (52 mg, 0.25 mmol) and NHS (29 mg, 0.25 mmol).

The NHS ester in THF (5 ml), following workup, was added to a stirring solution of BgG (500 mg, 2.86 mmol) in phosphate (pH=9.0) buffer and stirred at 4° for 24 h.

The reaction mixture was purified as previously described except that Sephadex chromatography was not carried out. Both the precipitate and supernatant were dialyzed against water/ammonium hydroxide (4×4 L) for 4 days then lyophilized to afford 312 mg and 134 mg [total=447 mg (79%)] respectively with hapten numbers of 30 and 32 respectively.

2.4 Conjugation of N-[3-(2'-acetylamino-5'-hydroxyphenyl-1')]propionyl glycine to Glucose-6-phosphate Dehydrogenase.

Conjugation of the compound prepared in Example 2.1 to G6PDH was achieved in a manner analogous to that described in Example 1.4, including the use of EDAC to activate the compound, the formation of the NHS ester, and conjugation with G6PDH using the G6P disodium salt and the NADH coenzyme, and desalting. The G6PDH used was Bionova Lot K02 treated with the protease inhibitor phenylmethylsulfonylfluoride.

Table II shows the progress of the conjugation Enzyme deactivation is shown as percent of that associated with the non-conjugated enzyme.

TABLE II

| G6PDH Conjugation of N—[3-(2'-Acetylamino-5'-hydroxyphenyl-1')]propionyl glycine | | | |
|---|---|---|---|
| Total Hapten Added (μl) | Hapten/Enzyme Mole Ratio | Enzyme Deactivation | Percent Inhibition |
| 4 | 23 | 7 | 19 |
| 16 | 99 | 34 | 62 |
| 26 | 153 | 48 | 72 |
| 36 | 213 | 59 | 76 |
| 45 | 268 | 67 | 77 |

3.1 Antisera Preparation

The antigens prepared above were injected into a series of sheep, using four sheep per antigen, and a series of bleeds were taken from each sheep. The bleeds were then tested for titer and those with the highest titer were employed in an immunoassay as described in U.S. Pat. No. 3,817,837 (Rubinstein et al., Syva Corporation, issued June 18, 1974), the contents of which are incorporated herein by reference. The following reagents were used in the assay:

Buffer: 0.055 M Tris-HCl (pH=8.1), 0.05% NaN$_3$, 0.005% thimerosal

Assay buffer: Buffer, 0.5% NaCl, 0.01% (volume basis) Triton ® X-100 (surfactant sold by Rohm and Haas Co.), pH=8.1

Antibody reagent: Buffer, 1.0% RSA, (G6P)Na 0.006M, NAD 0.04M, pH=5, quantity indicated Enzyme conjugate reagent: Buffer, 0.9% NaCl, 1.0% RSA, (G6P)Na, 0.033M pH=6.2, sufficient enzyme conjugate to provide $R_{max}$ as indicated Calibrators: 10, 25, 50, 100, and 200 μg/ml Control: 75 μg/ml Matrix: Dextran sulfate-treated human serum The assay protocol was as follows: a 50 μl sample is drawn up into a diluter and dispensed with 250 μl of the assay buffer into a one-ml Croan cup. A 50 μl aliquot of the diluted sample is drawn up and dispensed with a 250 μl portion of assay buffer into a second Croan cup. Into the latter is then introduced a sample of the antibody reagent of specified size and 250 μl of the assay buffer, followed by a sample of the enzyme conjugate reagent of sufficient size to achieve the specified $R_{max}$ and 250 μl of the assay buffer. Immediately thereafter, the entire sample is aspirated in a flow cell. A first reading is taken 15 seconds after aspiration, and a second reading is taken 45 seconds after aspiration. The results are reported as the difference in absorbance×2.667, minus the corresponding value achieved when no analyte is present (i.e., $R - R_o$).

Table III lists the results of three series of calibration tests, each using five samples spiked with increasing levels of acetaminophen. A different combination of acetaminophen analogs and antigen was used in each series. The antibodies in these tests were generated by injecting sheep with the indicated antigens according to conventional procedures, and taking a series of successive bleeds. The bleeds were then screened by reaction with enzyme conjugates and measurement of the resulting separations. The fifth bleed from each sheep showed the highest antibody concentration, and was therefore used in calibration runs.

TABLE III

Acetaminophen Assay Calibrations
Antibody sample size: 5 μl
Enzyme $R_{max} = 650$

| Acetaminophen Concentration (μl/ml) | $R - R_o$ Assay A* | Assay B | Assay C |
|---|---|---|---|
| 10 | 35 | 40 | 66 |
| 25 | 68 | 80 | 100 |
| 50 | 100 | 125 | 134 |
| 100 | 142 | 182 | 170 |
| 200 | 188 | 238 | 200 |

*Assay A: Antibody generated from (cpd. #1)-BgG antigen; enzyme conjugate: (cpd. #1)-G6PDH
Assay B: Antibody generated from (cpd. #2)-BSA antigen; enzyme conjugate: (cpd. #1)-G6PDH
Assay C: Antibody generated from (cpd. #2)-BgG antigen; enzyme conjugate: (cpd. #2)-G6PDH

3.2 Cross-reactivity Study

Cross-reactivity, or interference in the detection signal due to the presence of compounds other than acetaminophen binding to the antibody, was measured for five antibody/enzyme conjugate combinations at various dilutions. Compounds used as potential cross-reactants were acetylsalicylic acid (aspirin) and the sulfate, glucuronide, and cysteine metabolites of acetaminophen. The test consisted of performing an assay on the cross-reactant spiked into the 50 μg/ml calibrator to determine the concentration which produced the same signal as 65 μg/ml of acetaminophen. The results are shown in Table XIII, where micromolar (μM) units are used for the metabolites, since they are derived from acetaminophen (a 6.6 μM solution of which corresponds to 1.0 μl/ml), and μg/ml for acetylsalicylic acid. Antibodies were again generated by injecting sheep with the indicated antigens, and the fifth bleed was used in all tests except the next to last, where the sixth was used.

TABLE IV

| Antigen Used to Generate Antibody | Antibody Dilution | Enzyme Conjugate* | Cross-reactivity Acetylsalicylic Acid (μg/ml) | Sulfate (μM) | Glucuronide (μM) | Cysteine (μM) |
|---|---|---|---|---|---|---|
| #1-BgG | 1:250 | #1 | >1000 | >6600 | >6600 | >6600 |
| #1-BgG | 1:83 | #1 | >1000 | >6600 | >6600 | >6600 |
| #1-BSA | 1:125 | #1 | >1000 | >6600 | >6600 | >6600 |
| #2-BgG | 1:15.6 | #1 | >1000 | >6600 | >6600 | >6600 |
| #2-BgG | 1:31 | #1 | >1000 | >6600 | >6600 | >5300 |
| #2-BgG | 1:12.5 | #1 | >1000 | >6600 | >6600 | >6600 |
| #2-BgG | 1:5 | #1 | >1000 | >6600 | >6600 | 10 |
| #2-BSA | 1:6 | #1 | >1000 | >6600 | >6600 | >6600 |
| #2-BSA | 1:12.5 | #1 | >1000 | >6600 | >6600 | 00 |
| #2-BSA | 1:8.3 | #1 | >1000 | >6600 | >6600 | .25 |
| #2-BgG | 1:167 | #2 | >1000 | >6600 | >6600 | .30 |

*The enzyme G6PDH was used exclusively.

The ">" sign in the table indicates that the concentration shown was insufficient to produce a signal equal to that produced by 65 μg/ml of acetaminophen. It is clear from the table that cross-reactivity was negligible with a few exceptions.

A more extensive cross-reactivity study was then conducted on the combination of GPA-BgG antibody (Ex. 2.3) and AD-G6PDH conjugate (Ex. 1.4). This time the relative amounts were adjusted to provide $R_{max}=650$. In addition to the three metabolites, a wide variety of drugs were tested as well as the antidote N-acetyl-1-cysteine. The results are shown in Table XIV, indicating no detectable cross-reactivity. A sheep was again used to generate the antibody, and a blend of the seventh through eleventh bleeds was used.

TABLE V

| Class of Compounds | Compound | Cross-reactivity |
|---|---|---|
| Metabolites | acetaminophen-cysteine | >1000 μg/ml |
| | acetaminophen-glucuronide | >1000 μg/ml |
| | acetaminophen-sulfate | >1000 μg/ml |
| Drugs Having phenolic Structures | oxyphenbutazone | >1000 μg/ml |
| | synephrine | >1000 μg/ml |
| | pentazocine | >1000 μg/ml |
| | phenylephrine hydrochloride | >1000 μg/ml |
| | cyclazocine | >1000 μg/ml |
| | pholedrine | >1000 μg/ml |
| | phenazocine | >100 μg/ml |
| | phenacetin | >1000 μg/ml |
| Antidote | N—acetyl-1-cysteine | >1000 μg/ml |
| Others | naproxen | >1000 μg/ml |
| | cimetidine | >1000 μg/ml |
| | methadone | >1000 μg/ml |
| | scopolamine | >1000 μg/ml |
| | meperidine | >1000 μg/ml |
| | promethazine | >1000 μg/ml |
| | caffeine | >1000 μg/ml |

TABLE V-continued

| Class of Compounds | Cross-reactivity | |
|---|---|---|
| | Compound | Cross-reactivity |
| | naloxone | >1000 μg/ml |
| | morphine | >1000 μg/ml |
| | atropine | >1000 μg/ml |
| | codeine | >1000 μg/ml |
| | propoxyphene | >1000 μg/ml |
| | secobarbital | >1000 μg/ml |
| | chlorpromazine | >1000 μg/ml |
| | phencyclidine (PCP) | >1000 μg/ml |
| | benzoyl ecgonine | >1000 μg/ml |
| | cocaine | >1000 μg/ml |
| | dextromethorphan | >1000 μg/ml |
| | acetyl salicylic acid | >1000 μg/ml |

3.4 Comparison Against Other Analytical Techniques

A series of samples of human serum from patients were analyzed both by the method of the present invention and by high pressure liquid chromatography (HPLC) and by two commercially prepared colorimetric techniques for acetaminophen, Stanbio ® and Lancer ®. The results are shown in Table XV, where a close agreement is evident.

TABLE VI

| | Assay Comparison | | | |
|---|---|---|---|---|
| Sample No. | This Invention* | HPLC | Stanbio Colorimetry | Lancer Colorimetry |
| 1 | 119 | 118 | 146 | 130 |
| 2 | 16 | 14 | 47 | |
| 3 | 89 | 83 | 110 | 97 |
| 4 | 27 | 17 | 52 | |
| 5 | 20 | 18 | 26 | |
| 6 | 31 | 26.5 | 32 | |
| 7 | 2 | 3 | 5.5 | |
| 8 | 20 | 19 | 16.5 | |
| 9 | 2 | 3 | | |
| 10 | 3 | 3 | | |
| 11 | 1.5 | 0 | | |
| 12 | 119 | 103 | 121 | 109 |
| 13 | 116 | 104 | 113 | 106 |
| 14 | 72 | 67 | 82 | 62 |
| 15 | 109 | 100 | 116 | 99 |
| 16 | 78 | 71 | 73 | 63 |
| 17 | 48 | 41 | | |

*Using assay reagents listed for Table XIV.

Although the foregoing invention has been described in some detail by way of illustration and example for purposes of clarity and understanding, it will be obvious that certain changes and modifications may be practiced within the scope of the appended claims.

What is claimed is:

1. A compound of the formula

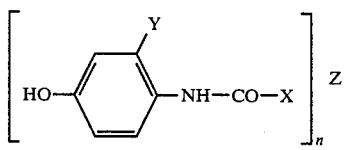

wherein:
X is methyl or $-R-(CO)_m$
Y is $-R^1-CO-NH-R^2(CO)_m$ when X is methyl, and hydrogen when X is $-R-(CO)_m$
R, $R^1$, and $R^2$ are independently aliphatic linking groups of from 1 to 12 carbon atoms each;
Z is a poly(amino acid) residue which is an enzyme;
m is zero or one; and
n is an integer ranging from one to a value approximately equal to the molecular weight of Z divided by 500 when Z is a poly(amino acid), and is otherwise one.

2. A compound of the formula:

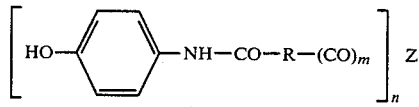

wherein:
R is a aliphatic linking froup of from 1 to 12 carbon atoms;
Z is a poly(amino acid) residue which is an enzyme;
m is zero or one; and
n is an integer ranging from one to a value approximately equal to the molecular weight of Z divided by 500 when Z is a poly(amino acid), and is otherwise one.

3. A compound according to claim 2 in which R is fully separated and has a straight-chain configuration.

4. A compound according to claim 2 in which R is fully saturated, has a straight-chain configuration, and contains from 2 to 8 carbon atoms.

5. A compound according to claim 2 in which R is fully saturated, has a straight-chain configuration, and contains from 3 to 6 carbon atoms.

6. A compound of the formula:

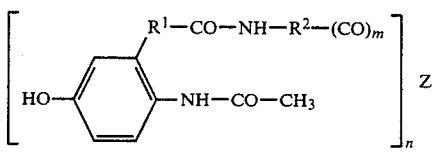

wherein:
$R^1$ is an aliphatic linking group of from 1 to 12 carbon atoms;
$R^2$ is an aliphatic linking group of from 1 to 12 carbon atoms;
Z is hydrogen, hydroxyl, alkoxyl of from 1 to 6 carbon atoms, or a group capable of forming an activated ester capable of amide formation with an amino acid in an aqueous medium, or a poly(amino acid) residue which is antigenic or an enzyme;
m is zero or one when Z is a poly(amino acid) residue, and is otherwise one; and
n is an integer ranging from one to a value approximately equal to the molecular weight of Z divided by 500 when Z is a poly(amino acid), and is otherwise one.

7. A compound according to claim 6 in which $R^1$ and $R^2$ are each fully saturated each has a straight-chain configuration.

8. A compound according to claim 6 in which $R^1$ and $R^2$ are each fully saturated, each has a straight-chain configuration, and each contains from 1 to 6 carbon atoms.

9. A compound according to claim 6 in which $R^1$ and $R^2$ are each fully saturated and each has a straight-chain configuration, and $R^1$ contains from 1 to 4 carbon atoms, and $R^2$ contains from 1 to 3 carbon atoms.

10. A compound according to claims 1, 2, or 6 in which Z in an enzyme having a molecular weight of from about 10,000 to about 1,000,000 daltons, and n ranges from about 2 to about 20.

11. A compound according to claims 1, 2, or 6 in which Z is glucose-6-phosphate dehydrogenase.

* * * * *

UNITED STATES PATENT AND TRADEMARK OFFICE
CERTIFICATE OF CORRECTION

PATENT NO. : 4,504,413
DATED : March 12, 1985
INVENTOR(S) : Pyare Khanna

It is certified that error appears in the above—identified patent and that said Letters Patent is hereby corrected as shown below:

Claim 1, Column 14, lines 1 and 2 after "by 500" delete --when B is a poly (amino acid), and is otherwise one--

Claim 2, Column 14, lines 17 and 18 after "by 500" delete --when B is a poly (amino acid), and is otherwise one--

Claim 6, Column 14, lines 41-44 after "B is" delete --hydrogen, hydroxyl, alkoxyl of from 1 to 6 carbon atoms, or a group capable of forming an activated ester capable of amide formation with an amino acid in an aqueous medium, or--

Claim 6, Column 14, line 45 after "which is" delete --antigenic or--;

Claim 6, Column 14, lines 50 and 51 after "by 500" delete --when B is a poly(amino acid), and is otherwise one--.

Signed and Sealed this

Eighth Day of October 1985

[SEAL]

Attest:

Attesting Officer

DONALD J. QUIGG

Commissioner of Patents and Trademarks—Designate